United States Patent [19]

Grimm

[11] Patent Number: 4,762,515

[45] Date of Patent: Aug. 9, 1988

[54] MEDICAMENT IMPLANT APPLICATOR

[75] Inventor: C. Louis Grimm, Shawnee, Kans.

[73] Assignee: Ivy Laboratories, Inc., Overland Park, Kans.

[21] Appl. No.: 754

[22] Filed: Jan. 6, 1987

[51] Int. Cl.$^4$ ............................................. A61M 31/00
[52] U.S. Cl. ........................................ 604/61; 74/411; 604/63
[58] Field of Search .................................. 604/59–64, 604/134, 135; 74/411; 464/40, 59, 160; 128/330

[56] References Cited

U.S. PATENT DOCUMENTS

| 2,632,444 | 3/1953 | Kas ........................................ 604/62 |
| 2,883,984 | 4/1954 | Candido, Jr. et al. ................. 604/62 |
| 3,529,704 | 9/1970 | Winstone et al. ...................... 464/59 |
| 4,447,223 | 5/1984 | Kaye et al. ............................ 604/61 |
| 4,474,572 | 10/1984 | McNaughton et al. .............. 604/61 |
| 4,576,591 | 3/1986 | Kaye et al. ............................ 604/61 |
| 4,687,465 | 8/1987 | Prindle et al. ........................ 604/61 |

Primary Examiner—C. Fred Rosenbaum
Assistant Examiner—H. Macey
Attorney, Agent, or Firm—Morris Fidelman; Franklin D. Wolffe

[57] ABSTRACT

In pistol grip medicament implanter devices, wherein a trigger coupled to a plunger causes plunger advance movement that expels the medicament from the device when the trigger is pulled, a spring that forms part of the coupling and a lost motion arrangement controlled by the spring that converts trigger pull movement into spring take-up of the trigger movement when the plunger encounters resistance to advance movement greater than the spring bias. The trigger continues to move but the plunger does not, then when resistance to movement of the plunger becomes less than the spring bias, the spring force serves to advance the plunger, recovering the trigger pull motion previously lost.

The greatest force that can be applied by the plunger to the medicament implant has become whatever bias is selected for the spring.

6 Claims, 4 Drawing Sheets

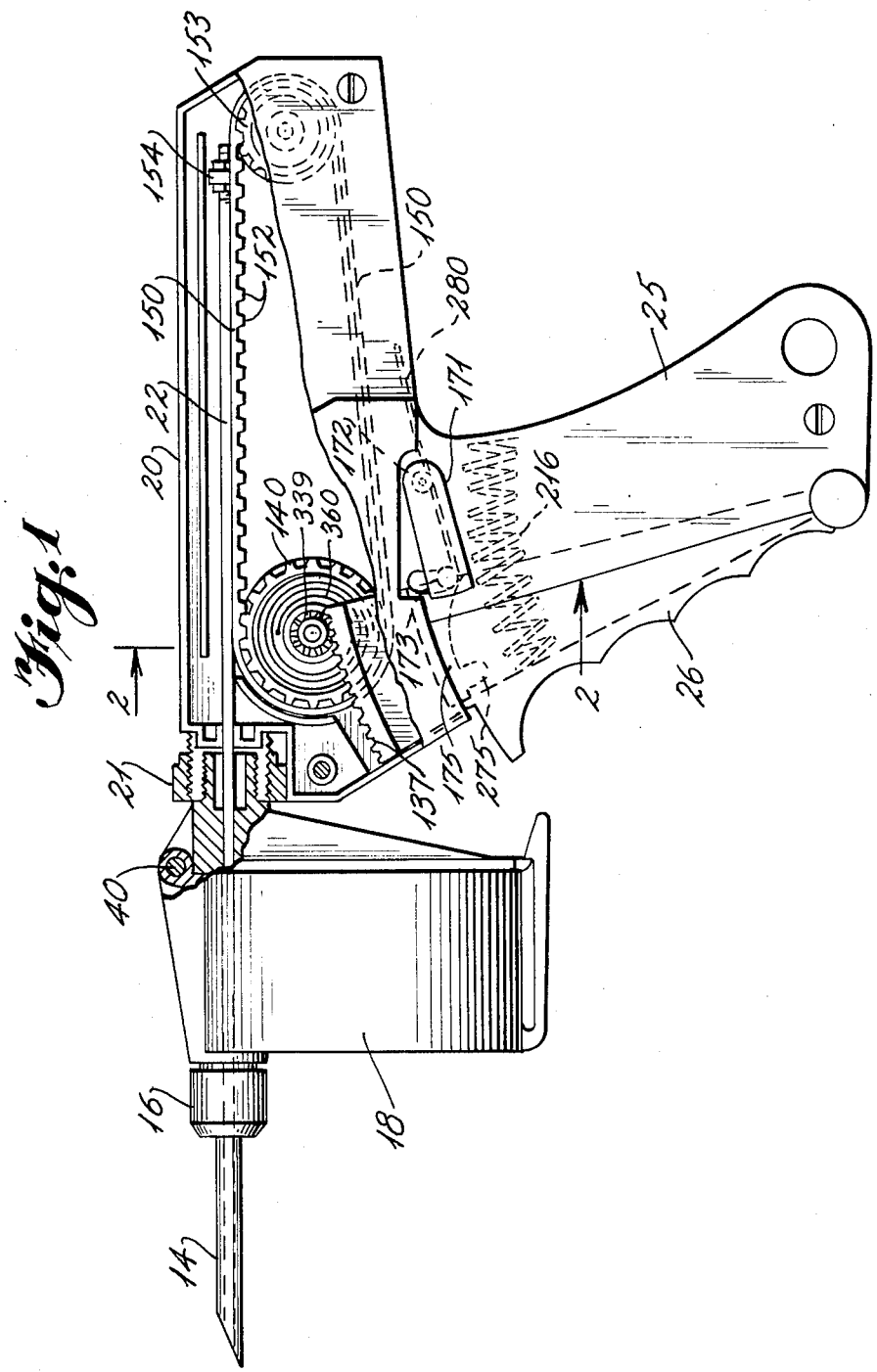

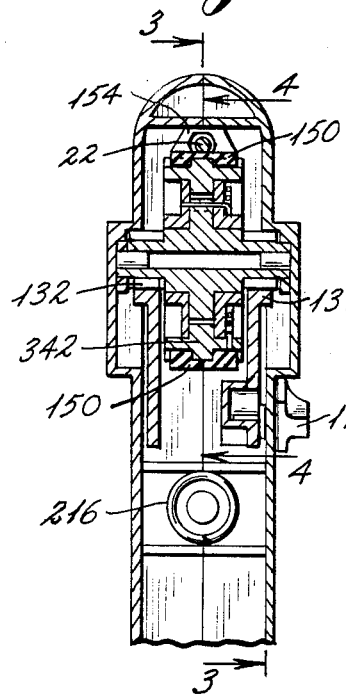
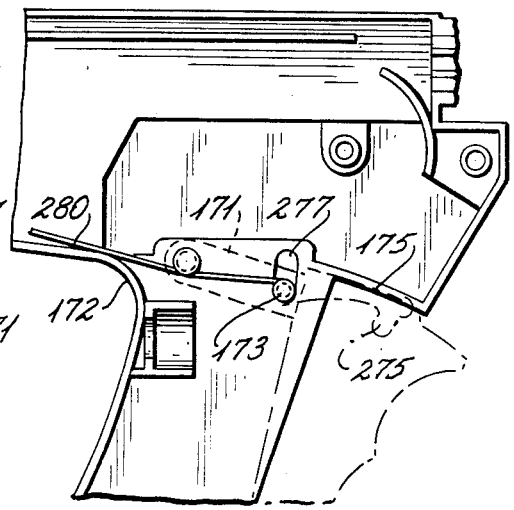
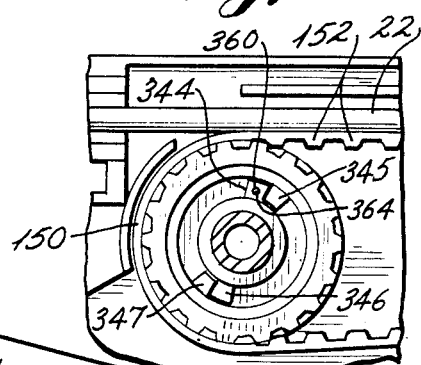
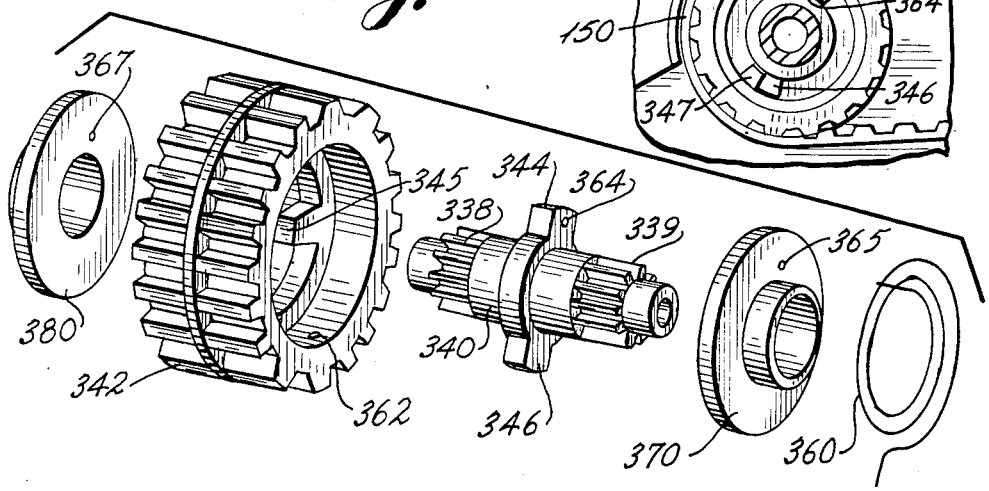

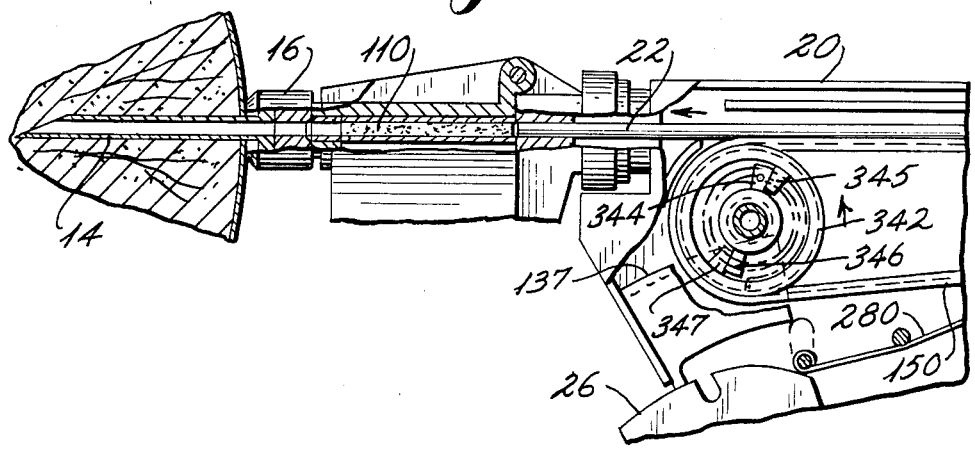
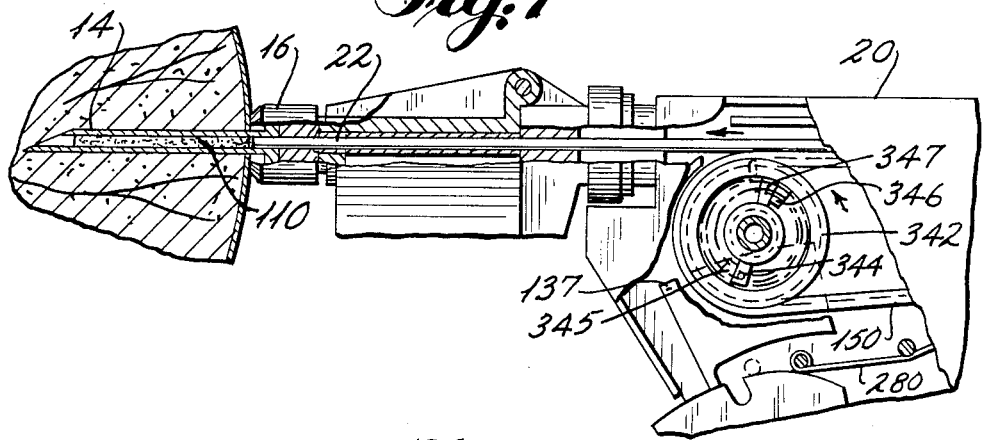
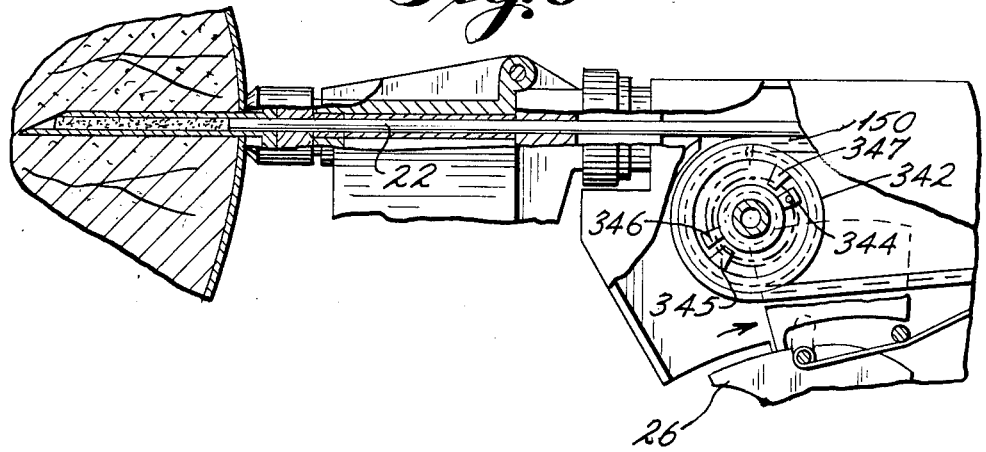

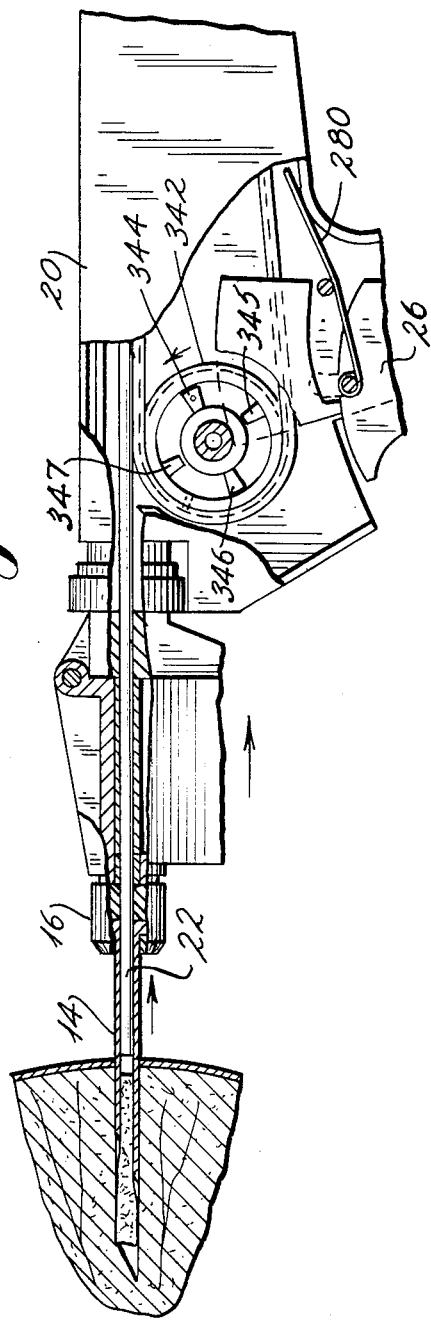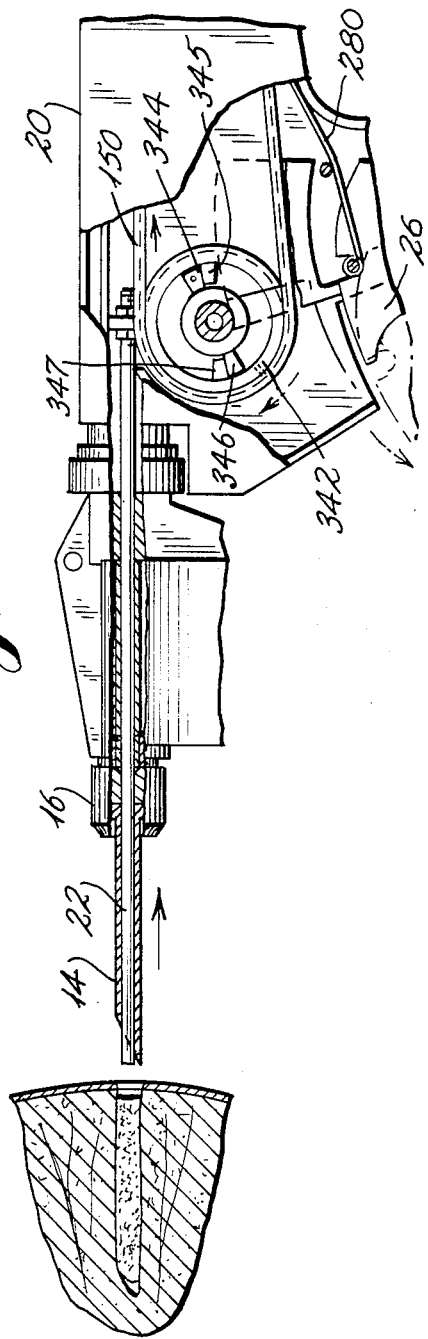

MEDICAMENT IMPLANT APPLICATOR

The present invention relates to an implanter device adapted for insertion of a solid or semi-solid pellet form medicament into a domestic animal.

INTRODUCTION

Good animal husbandry practices sometimes require insertion into the animal (e.g., intradermally, subcutaneously, intramuscularly, etc.) of a solid or semisolid medicament. Such practice is common for growth stimulation of cattle, for example. Solid or semi-solid pellets containing the growth stimulating hormones are implanted in the neck or ear of the animal, to remain there for an extended period, even throughout the lifespan of the animal. The ear is a preferred implantation site, since the ear is a throwaway organ. Any implant residue present in the ear when the animal is slaughtered never enters channels of commerce, to become ingested by people or domestic animals.

A typical medicament implanter device comprises a hand-held instrument built of a size consistent with the size of the animal (large for cattle, small for chickens). An apertured needle on the instrument makes a sizable, non-coring puncture opening into the skin e.g., of the ear of the animal and forms a cavity in the skin occupied temporarily by the needle on the instrument. The needle of the implanter is inserted into the skin of the animal, then withdrawn. As the needle is being withdrawn from the animal, pellets of medicament are expelled into the cavity formed by the needle.

For cattle, an implant dosage unit form may constitute a multiplicity, e.g., eight relatively small solid or semi-solid pellets. A reciprocal plunger inside the body of the implanter forces the pellet dosage unit out of a cartridge encasement wherein they were prepackaged into the bore of the needle and from there into the animal.

A number of medicament implant devices have been suggested to the art, including devices adapted for use with cartridges or other encasement forms that contain a multiplicity of dosage units of the implants, U.S. Pat. No. 3,774,607, for example. This invention relates to the multi-dose aspect of the medicament implanter art and, in particular, to the pistol-like devices suggested to this art.

When carefully and properly used, the pistol grip multi-dose applicators, particularly the applicator described in U.S. Pat. No. 4,576,591, have had satisfactory use experience. However, an exact proper implanting technique has turned out to be required. If the user of the applicator is inexperienced, tired or rushed, (when technique becomes less exact), implantation results suffer. Pellets break; not all of the pellets are implanted; sometimes a pellet is left at the needle exit hole, the last increasing the possibility of infection at the implant site.

Proper implanting of medicament pellets requires that the medicament pellets be deposited in the needle track while the needle is being withdrawn. (An impeller inside the applicator pushes the pellets through the needle out into the needle track.) If withdrawal of the needle commences, then is reversed, e.g., because of jerking movement by the animal, the result is likely to be pellets jammed together. If the needle is withdrawn too quickly, all of the pellets will not be expelled soon enough; a pellet might be left in the needle exit hole, or not implanted.

The object of this invention is to provide an implant applicator wherein the applicator structure compensates for inexact implanting technique, reducing thereby the incidence of breakage and misalignment of the implant pellets.

BRIEF STATEMENT OF THE INVENTION

In brief, the improvement of this invention comprises imposing of a spring bias on the impeller of a pistol grip implant applicator. The spring force supplements or replaces the tactile feel experienced by the user during operation of the implant applicator.

In normal operation of the implanter, the user inserts the needle completely, then operates the impeller, i.e., pulls the trigger of a pistol grip applicator. The force of trigger pull generates the impeller movement that transposes the implant pellets into, then through the needle, giving the user a tactile feel of low resistance to trigger movement while the pellets are being pushed into the needle, and then high resistance to trigger movement when the first pellet reaches the front end of the needle. Thereafter, good implanting practice requires the user to withdraw the needle while still squeezing the trigger to advance the impeller so that the pellets are laid down in the needle track.

In practice of this invention, a spring bias is imposed on the impeller so that the spring will become compressed or wound to at least some middle level of the spring capability by high resistance to trigger movement which happens when the implants reach the front end of the needle (abutting unpenetrated flesh). Then the spring bias on the impeller generates lost motion which adjusts for the heavy-handed user who would otherwise push pellets faster than the needle retracts, by converting trigger movement into spring movement, compressing or winding up the spring. The spring force on the impeller adjusts for the overeager user who would withdraw the needle quicker than the impeller advances by generating impeller movement (in recovery of the lost motion) from relaxation of the spring.

By and large, the spring force determines the maximum pressure applied to the pellets by the impeller and is the cause of their expulsion. The tactile feel experienced by the user is one of resiliency, the spring resiliency, in fact. When the pellets encounter the solid flesh, the spring takes up the trigger force. Only, when, as, and if the lost motion limit has been reached, does the user experience the high resistance feel of unpenetrated flesh. Desirably, the lost motion limit exceeds the length of a pellet dosage unit so that the pellets experience only the spring force, i.e. a controlled force less than the pellet crush limit. Then as the pellets are being expelled during withdrawal of the needle to leave the pellets in the needle track, the feel of resiliency advises the user that implantation is proceeding properly. The spring resiliency reduces the incidence of pellet breakage and misalignment.

In an optional embodiment of the invention, the trigger becomes latched in pulled position. The user can pull the trigger to the fullest, then rely entirely upon spring force to expel pellets while the needle is being withdrawn.

DISCUSSION OF THE INVENTION

Further explanation of the invention and a detailed discussion thereof is provided below in the context of a preferred embodiment exemplary mode implanter containing the spring biasing and temporarily lost motion.

A widely used state-of-the-art pistol grip implant applicator has been selected for exemplary purposes, i.e., the applicator described in U.S. Pat. No. 4,576,591, reference being made to that Patent and to its parent, U.S. Pat. No. 4,531,938, for any detail features incompletely provided herein.

Reference is now made to the drawings wherein:

FIG. 1 is a side view, partially in section, of the implant applicator in a closed position;

FIG. 2 is a partial end section taken along line 2—2 on FIG. 1;

FIG. 3 is a side section taken along line 3—3 on FIG. 2;

FIG. 4 is a partial side section taken along line 4—4 of FIG. 2 showing the combination gear which drives the plunger of the implant applicator;

FIG. 5 is an exploded diagrammatic view of the combination gear;

FIGS. 6 through 10 are each a partial side section of the implant applicator and together illustrate the course of an implanting sequence.

As may be seen in FIG. 1, the pistol grip implant applicator herein illustrated is a multi-part hinged structure split at a hinge 40 into the forward end needle sub-assembly described in U.S. Pat. Nos. 4,351,938 and 4,576,591, to which reference has already been made for the details not described herein, and the pistol grip and barrel sub-assembly described in U.S. Pat. No. 4,576,591, to which reference has already been made for any details not described herein. Although the modifications made in the pistol grip and barrel subassembly pursuant to the improvement of this invention are not readily apparent in FIG. 1, appreciation of the implanter structure is believed to be necessary for complete understanding of this invention. Thus, the applicator comprises front to rear, a hollow needle 14 secured by chuck 15 to the front of drum 18. Drum 18 contains the medicament supply therein. To the rear of drum 18 is the pistol grip and barrel 20.

The piston grip and barrel 20 secured to the rear of drum 18 by nut 21 is aligned to needle 14 so that the impeller or plunger 22 is centered for movement through drum 18 into needle 14. Forward movement of plunger 22 is generated by pulling or squeezing trigger 26 against the force of compression spring 216. Sector gears 132 and 137 (only the latter being visible in FIG. 1) on trigger 26 rotate combination gear 140 counterclockwise. Combination gear 140 meshes with and drives an endless belt 150 mounted between the combination gear 140 and an idler sprocket 153, belt 150 containing on the underside thereof, a multiplicity of spaced-apart teeth 152 that engage with combination gear 140 and idler sprocket 144. The plunger 22 is attached to endless belt 150 at a cutout 154 on the belt and rides on belt 150 during advancing and retracting movement.

Illustrated in FIG. 1 is an optional feature of the present invention, namely, a latch mechanism to lock the trigger 26 in its squeezed position so that compression spring 216 is unable to cause return movement of the trigger. As may be seen in FIG. 1, and more clearly in FIG. 3, a horizontal latch member 171 on the side of the pistol grip with a rear pin portion 172 pivotally seats on one side face of the pistol grip. On the free forward end of latch member 171 is a retainer button portion 173 that rides in a longitudinal recess 175 on trigger 26 while trigger 26 is being squeezed. At the forward end of recess 175 is a detent slot 275 and correspondingly a slot 277 is present in the side of the pistol grip so that retainer button portion 173 can ride recess 175, then pivot into detent slot 275 & lock trigger 26 in its fully squeezed position. A spring 280 biasing button portion 173 toward butt end of the pistol grip causes the button portion to ride against the lower rim of slot 277 and down into detent slot 275. The free end of latch member 171 must be forced up (e.g., by the holder's thumb) to release trigger 26, whereupon spring 216 impels trigger return and accordingly retraction of plunger 22. The latch mechanism is believed to constitute a major convenience for the user. Operator fatigue over extended use is reduced since the operator no longer must keep the trigger fully squeezed until the needle has been removed.

Illustrated principally in FIGS. 2, 4 and 5 is the spring bias structure of this invention. Mention has already been made that the sector gears 132 and 137 at the top of trigger 26 drive a combination gear 140. The portion of combination gear 140 which meshes with sector gears 132 and 137 is pinion gear 338 and 339. Pinion gears 338 and 339 drive a bull gear 342. The bull gear meshes with and drives the belt 150 (see FIG. 4). As may be seen in the exploded view of FIG. 5, pinion gears 338 and 339 are at the ends of a shaft 340 on which is disposed a pair of shoulders 344 and 346. On the inside surface of the (annular) bull gear 342, are a pair of ribs 345 and 347.

In the fully assembled combination gear 140, shoulders 344 and 346 and ribs 345 and 347 occupy the same plane. Normally, they abut, as is shown in FIG. 4. When rotation of the pinion gears 338 and 330 causes shaft 340 to rotate (counterclockwise in FIG. 4, the arrow direction) bull gear 342 need not rotate until shoulder 344 turns (nearly 180°) to abut against rib 347 Then, of course, further rotation of the pinion gears 338 and 339 rotate the bull gear 342. This spring biased temporarily lost motion is provided for generating the spring resiliency aspect of this invention. Desirably, the extent of plunger motion lost exceeds the length of the pellet dosage unit e.g., 1 3/16". Once so much motion is lost, the pellets can never encounter a force from the impeller in excess of the spring bias on the impeller.

A coil spring 360 is pinned at one end thereof in an aperture 362 on the inside rim wall of bull gear 342 and at the other end thereof in an aperture 364 on shoulder 344. A pair of rotatable washers 370 and 380 abut shoulders 344 and 346, one at each side face. The spring end in shoulder aperture 364 passes through apertures 365 and 367 on the retainer washers 370 and 380. The main body of spring 360 is coiled against the outside face of washer 370 around the inside rim wall of bull gear 342 imposing a spring bias sufficient to overcome low resistance to movement of plunger or impeller 22. Spring 360 is relatively stiff; squeezing trigger 26, which rotates pinion gears 338 and 339, will rotate bull gear 342 until the impeller 22 encounters high resistance against further advancement, i.e., encounters solid flesh. High resistance to impeller movement overcomes the bias of spring 360 and then lost motion as alluded to above takes place as shoulder 344 rotates away from rib 345, winding up spring 360. In the illustrated mode of the invention, a limit for trigger movement is reached (just) before shoulder 344 abuts rib 346. By then, trigger motion is sufficient for latch 171 to lock trigger 26 against return motion.

When resistance to impeller advancement decreases, as happens when withdrawal of needle 14 commences, spring 360 can begin to unwind by moving bull gear 342 through the connection of bull gear and spring at aperture 362, rotating bull gear 342 (in the arrow direction) to advance impeller 22 and recover the lost motion. Since impeller 22 is advancing during withdrawal of needle 14, the medicament pellets are reliably deposited in the needle track.

The operational attributes of the improved implanter is diagrammatically illustrated by FIGS. 6 through 10. Referring now to FIG. 6, it may be seen that just before trigger 26 is pulled, shoulder 344 is biased by spring 360 against rib 345 and impeller 22 is entirely inside barrel and grip 20; needle 14 has been inserted in the animal at the site desired for implantation of medicament pellets 110. Then squeezing of trigger 26 causes impeller 22 to advance. Movement of the pellets into needle 14 is low resistance motion. Since the spring bias is not overcome by the resistance encountered in transfer of the medicament pellets into needle 14, shoulder 344 remains biased against rib 345, as is shown in FIG. 7. However, resistance to expulsion of the medicament pellets from needle 14 against the relatively solid animal flesh ahead of needle 14, overcomes the spring bias, so that (further) squeezing of trigger 26 to the full extent, where latch retainer button 173 drops into detent slot 275, causes lost motion rotation only of the pinion gear; shoulders 344 and 346 rotate away from ribs 345 and 347. Spring 360 winds up as bull gear 342 remains stationary, as is illustrated in FIG. 8. The user can sense the spring winding up.

When needle 14 is withdrawn from the animal the spring 360 unwinds, turning bull gear 142 which advances impeller 22 to force the medicament pellets into the needle track, as is illustrated in FIG. 9. Finally, impeller 22 becomes fully advanced, at which time all the medicament pellets 110 have been expelled in the needle track. Thus, all of the pellets are deposited inside the animal's skin, as is illustrated in FIG. 10. Spring 360 has unwound until shoulder 344 is again abutting rib 345 in full recovery of the lost motion. A subsequent release of latch 171 allows return of trigger 26 retracting impeller 22 to its rest position.

FIG. 10 illustrates how the spring resiliency feature of the present invention allows the impeller 22 to be extended beyond the needle tip e.g., ⅜", insuring thereby that all pellets have cleared the needle. Usual concerns about impeller length and pellet crushing are obviated by making spring resiliency force the pressure limit.

It is emphasized that presence of the trigger latching mechanism is optional and not preferred. Omission of the latch feature simplifies construction of the implanter. Also, many experienced users of the implanter prefer an implanter without the latch feature.

I claim:

1. In a pistol-like medicament implanter comprising:
   (a) a hollow needle and a plunger means in axial alignment, said plunger means being movable into said hollow needle;
   (b) storage means for at least one medicament implant dosage unit interposed between said needle and said plunger means, such dosage unit being disposed in a passthrough chamber indexed in line with said needle and said plunger means whereby said plunger means may travel through the indexed dosage unit chamber to expel the medicament therefrom; and
   (c) a trigger means operatively connected to said plunger means so that when said trigger means is pulled, said plunger means advances through said chamber into the bore of said needle expelling thereby the implant dosage unit therefrom, and thereafter retracts when said trigger means is released;
   the improvement which comprises a spring forming part of the operative connection between said trigger means and said plunger means, said spring being disposed to transmit the trigger pull movement to said plunger means so as to advance same, the bias of said spring being set so that when resistance to advance of said plunger means exceeds the spring bias any pulling movement on said trigger means results in spring take-up and lost motion by said trigger means, whereby a subsequent reduction in resistance to advance of said plunger means generates a spring impelled advance of said plunger means with consequent spring relaxation and there through recovery of the motion lost by said trigger means, the spring force thereby serving to generate the implant expelling movement by said plunger means.

2. The implanter device of claim 1 wherein the extent of plunger movement preventable by spring take-up exceeds the length of a medicament implant dosage unit.

3. The implanter device of claim 2 wherein the plunger means advances to beyond the hollow needle.

4. The implanter device of claim 2 further comprising releasable latch means locking said trigger means in pulled position.

5. The implanter device of claim 1 further comprising a releasable latch positioned to lock said trigger means in its fully pulled position.

6. In a pistol-like medicament implanter comprising:
   (a) a hollow needle and a plunger means in axial alignment, said plunger means being movable into said hollow needle;
   (b) storage means for at least one medicament implant dosage unit interposed between said needle and said plunger means, such dosage unit being disposed in a passthrough chamber indexed in line with said needle and said plunger means whereby said plunger means may travel through the indexed dosage unit chamber to expel the medicament therefrom; and
   (c) a trigger means operatively connected to said plunger means so that when said trigger means is pulled, said plunger means advances through said chamber into the bore of said needle expelling thereby the implant dosage unit therefrom, and thereafter retracts when said trigger means is released;
   the improvement which comprises a combination gear in the operative connection between said trigger means and said plunger means, one part of said combination gear being connected to drive said plunger means and another part being connected to be driven by said trigger means, the two said parts of said combination gear being joined by a coil spring disposed so as to cause conjoint movement of said gear parts whereby pulling movement of said trigger means generates advance of said plunger means, the bias of said spring being set so that when resistance to advance of said plunger means exceeds the spring bias, said coil spring winds up upon trigger pull movement without causing movement of the combination gear part that drives said plunger means whereby a subsequent reduction of resistance to advance by said plunger means allows unwinding of said coil spring with consequent spring impelled movement of the combination gear part that drives said plunger means, the spring force thereby serving to generate the implant expelling movement by said plunger means.

* * * * *